US00PP35604P2

(12) United States Plant Patent
Nelson

(10) Patent No.: US PP35,604 P2
(45) Date of Patent: Jan. 30, 2024

(54) COLORADO BLUE SPRUCE TREE NAMED 'HYMES BLUE DREAM'

(50) Latin Name: ***Picea pungens* var. *glauca***
Varietal Denomination: Hymes Blue Dream

(71) Applicant: Randall S. Nelson, Forest Grove, OR (US)

(72) Inventor: Randall S. Nelson, Forest Grove, OR (US)

(73) Assignee: TREESAP FARMS LLC, Houston, TX (US)

( * ) Notice: Subject to any disclaimer, the term of this patent is extended or adjusted under 35 U.S.C. 154(b) by 0 days.

(21) Appl. No.: 18/205,003

(22) Filed: Jun. 2, 2023

(51) Int. Cl.
*A01H 7/00* (2006.01)
*A01H 6/00* (2018.01)

(52) U.S. Cl.
USPC ..... Plt./213
CPC ..... *A01H 6/00* (2018.05)

(58) Field of Classification Search
USPC ..... Plt./213
CPC ..... A01H 7/00
See application file for complete search history.

*Primary Examiner* — Kent L Bell
(74) *Attorney, Agent, or Firm* — Penny J. Aguirre

(57) ABSTRACT

A new cultivar of Colorado blue spruce tree named 'Hymes Blue Dream' characterized by its foliage that is very intensely blue in color in appearance during the summer months and blue grey in color in the winter months, its foliage with a very glaucous surface, its dense and compact plant habit, and its short height; obtaining a height of 6 m in 20 years when grown in Oregon.

2 Drawing Sheets

Botanical classification: *Picea pungens* var. *glauca*.
Varietal denomination: 'Hymes Blue Dream'.

CROSS REFERENCE TO A RELATED APPLICATION

This application is related to a U.S. Plant Patent Application filed for a plant derived from the same Inventor that is entitled Colorado Blue Spruce Tree Named 'Ward's Blue Waves' (U.S. Plant patent application Ser. No. 18/205,004).

BACKGROUND OF THE INVENTION

The present invention relates to a new and distinct cultivar of *Picea pungens* var. *glauca* and will be referred to hereafter by its cultivar name, 'Hymes Blue Dream'. 'Hymes Blue Dream' represents a new cultivar of Colorado blue spruce, an evergreen plant grown for landscape use.

The inventor discovered 'Hymes Blue Dream' as a chance seedling in October of 2001 that was growing in a production field planted with unnamed plants of *Picea pungens* var. *glauca* at his nursery in Forest Grove, Oregon. The parent plants are therefore unknown.

Asexual propagation of the new cultivar was first accomplished by grafting in Forest Grove, Oregon in winter of 2002 under the direction of the Inventor. Asexual propagation by grafting has determined that the characteristics of this cultivar are stable and are reproduced true to type in successive generations.

SUMMARY OF THE INVENTION

The following traits have been repeatedly observed and represent the characteristics of the new cultivar. These attributes in combination distinguish 'Hymes Blue Dream' as a unique cultivar of *Picea*.

1. 'Hymes Blue Dream' exhibits foliage that is very intensely blue in color in appearance during the summer months and blue grey in color in the winter months.
2. 'Hymes Blue Dream' exhibits foliage with a very glaucous surface.
3. 'Hymes Blue Dream' exhibits a dense and compact plant habit.
4. 'Hymes Blue Dream' exhibits a short height; obtaining a height of 6 m in 20 years in Oregon.

The unnamed plants of *Picea pungens* var. *glauca* growing in the area of discovery differ from 'Hymes Blue Dream' in having more open and upright growth habits and dark green to dark gray color foliage, less compact plant habits, longer stem internodes, and in being much taller in height. 'Hymes Blue Dream' can be most closely compared to the cultivar 'Apache' (not patented) and 'Ward's Blue Waves'. 'Apache' differs from 'Hymes Blue Dream' in having less glaucous foliage, longer internodes, a less compact plant habit, and a taller plant height. 'Ward's Blue Waves' is similar to 'Hymes Blue Dream' in having a compact plant habit, a short plant height, and intense blue foliage in summer. 'Ward's Blue Waves' differs from 'Hymes Blue Dream' in having foliage that is silvery blue in color year around and in having branch apexes that curve upward.

BRIEF DESCRIPTION OF THE DRAWINGS

The accompanying color photographs illustrate the overall appearance and distinct characteristics of the new *Picea*. The photographs were taken of 21-year-old trees as grown in the ground in Forest Grove, Oregon.

Figure 1:
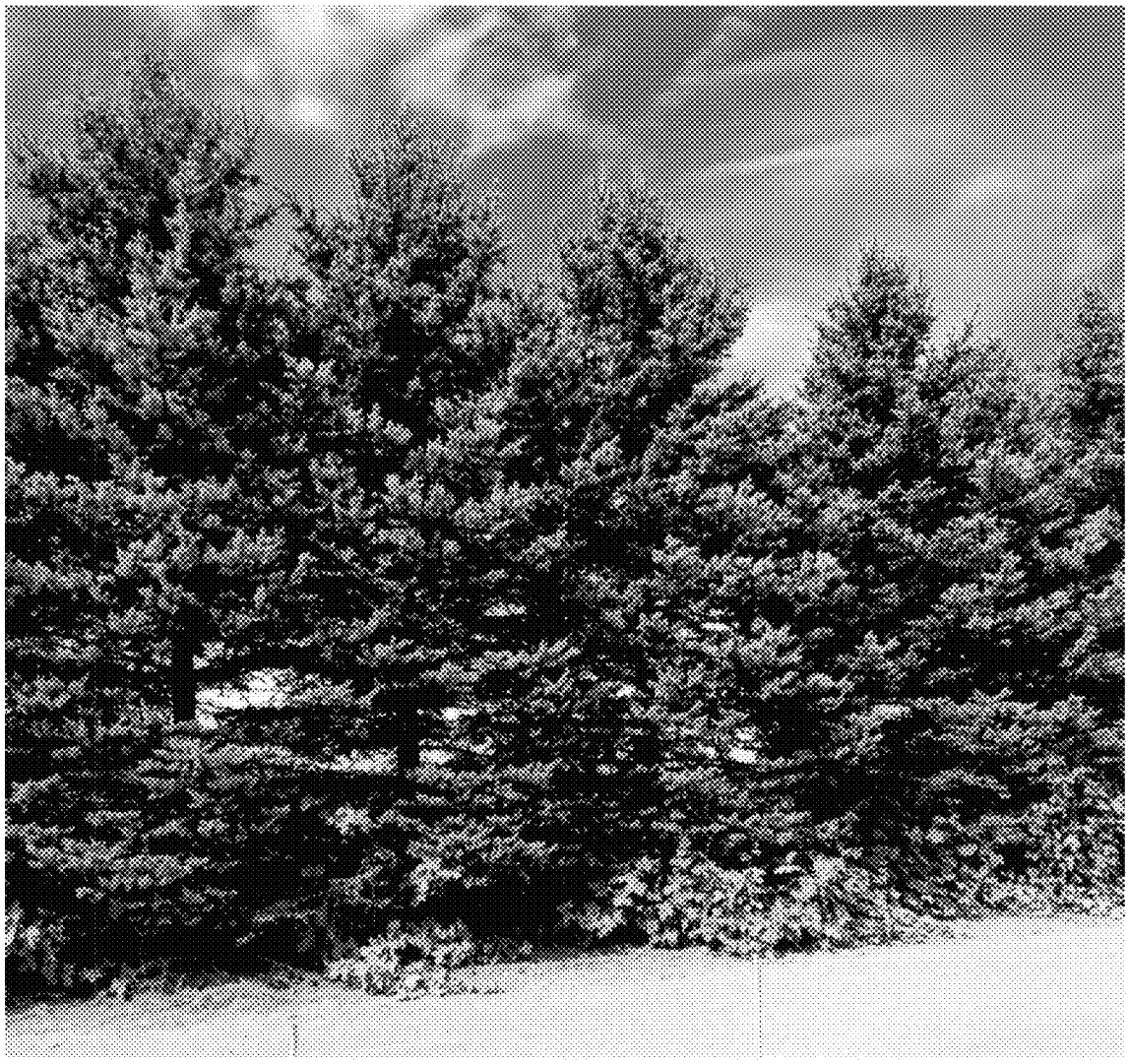
FIG. 1 provides an overall view of the plant habit of several trees of 'Hymes Blue Dream'.
Figure 2:
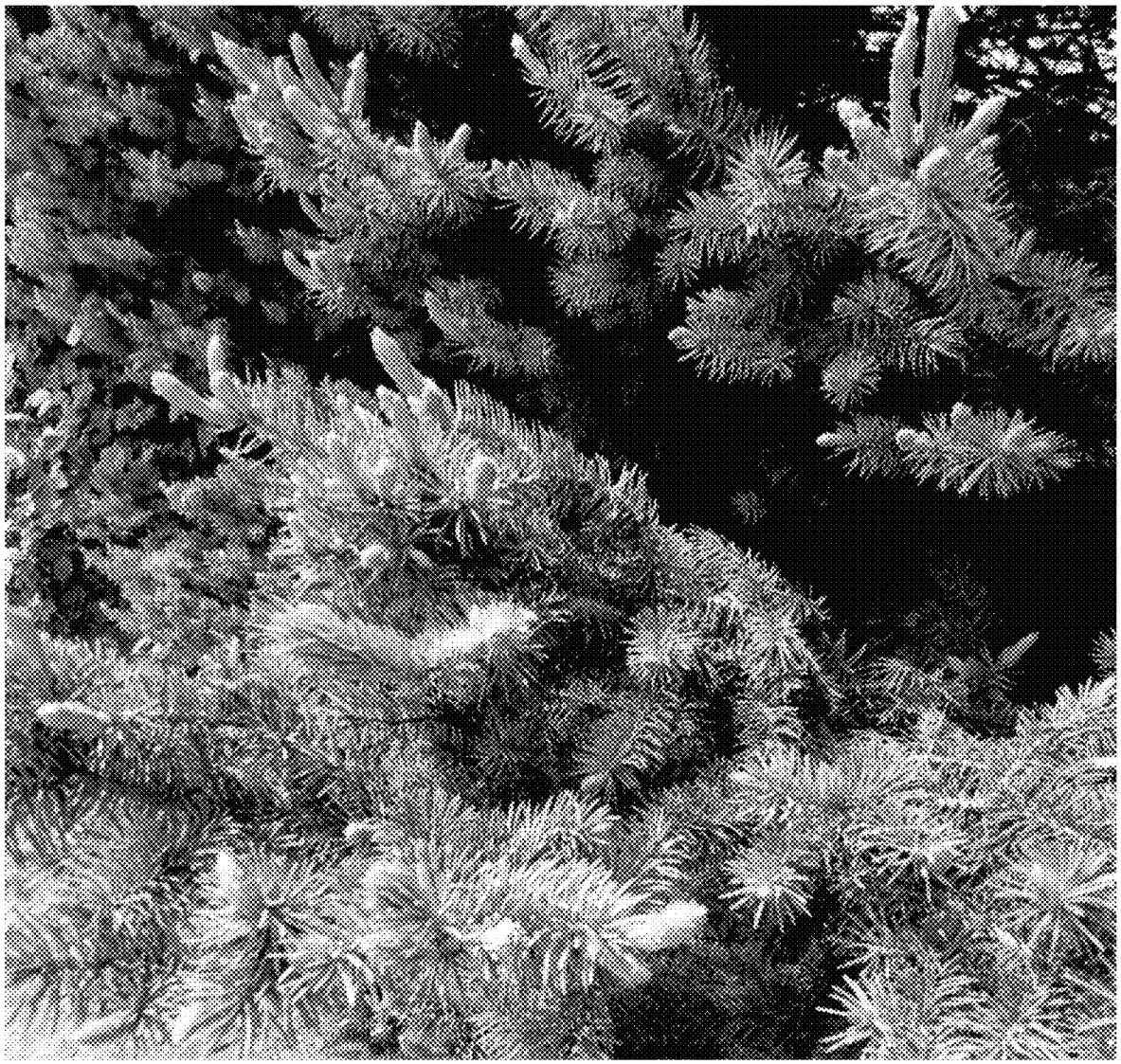
FIG. 2 provides a close-up view of the foliage of 'Hymes Blue Dream' in summer.

The colors in the photographs are as close as possible with the photographic and printing technology utilized. The color values cited in the detailed botanical description accurately describe the colors of the new *Picea*.

DETAILED BOTANICAL DESCRIPTION

The following is a detailed description of the new cultivar as taken from 2-year-old trees grown in 1-gallon nursery containers in Forest Grove, Oregon. The phenotype of the new cultivar may vary with variations in environmental, climatic, and cultural conditions, as it has not been tested under all possible environmental conditions. The color determination is in accordance with the 2015 Colour Chart of The Royal Horticultural Society, London, England, except where general color terms of ordinary dictionary significance are used.

General description:

*Plant type.*—Coniferous evergreen.

*Growth habit.*—Dense, conical, short, compact.

*Height and spread.*—An average of 44 cm in height and 29 cm in width as grown in a one-gallon container, reaches 4.6 m in height and 3.7 m in spread as a 10-year-old plant in the landscape, reaches 6.1 m in height in 20 years in the landscape.

*Cold hardiness.*—At least in U.S.D.A. Zone 3.

*Diseases and pests.*—No susceptibility or resistance to pests or diseases has been observed.

*Root description.*—Fibrous, moderately branched, moderately thick, a blend of N199B and N199C in color.

*Growth rate.*—Moderate.

*Propagation.*—Grafting.

*Root development.*—Grafted in late winter with final scion successfully grafted in approximately 20 weeks, time required to produce a young tree; 12 months.

Branch description:

*Trunk and branch shape.*—Rounded.

*Branch size.*—Main trunk; 17 cm in length, 2 cm in diameter, lateral branches; average of 14 cm in length, up to 3 cm in width, tertiary branches; up to 3 cm in length, 2 mm in width.

*Stem surface.*—Young stems; smooth, matte, linear streaks cover the surface, mature and old wood; rugose, bark-like and matte.

*Branching.*—Average of 11 lateral branches, 2 tertiary branches per lateral, strong central leader.

*Stem arrangement.*—Lateral branches; whorled to opposite, tertiary branches; opposite.

*Stem aspect.*—Strong, main stem vertical, lateral and tertiary stems held in a slightly upright angle.

*Internode length.*—Average of 1 to 3 cm.

*Stem color.*—Young stems; striations of 174A and 164B, mature stems; close to 161A, but lighter, old wood; blend of 164B, 165A and 165C.

*Resin glands.*—None observed.

Foliage description:

*Leaf arrangement.*—Densely whorled needles.

*Leaf attachment.*—Sessile.

*Leaf shape.*—Acicular, needle shaped.

*Leaf division.*—Simple.

*Leaf base.*—Cuneate.

*Leaf apex.*—Sharp and pointed, linear.

*Leaf venation.*—Not visible.

*Leaf margins.*—Entire.

*Leaf fragrance.*—When crushed, it produces a pine-like fragrance.

*Leaf surface.*—Upper surface; matte, lower surface; glossy, both surfaces highly glaucous.

*Leaf color.*—Emerging 138C, summer with sun exposure N138B with heavy glaucous coating of N155A, shaded and winter 139A with glaucous coating of 190D.

*Leaf texture.*—Dense, stiff and strong.

*Leaf aspect.*—Vertical to slightly bowed to branch.

*Leaf size.*—An average of 1.5 cm in length and 2 mm in diameter.

*Leaf quantity.*—Average of 200 per branch 14 cm in length.

*Leaf buds.*—5 mm in length and 2 mm in width, a blend of 166B and 165C in color, comprised of imbricate scales orbicular and cupped in shape and average of 2 mm in length and width.

Cone description: Cones have not been observed to date.

It is claimed:

1. A new and distinct cultivar of Colorado Blue Spruce tree named 'Hymes Blue Dream' as herein illustrated and described.

* * * * *